(12) United States Patent
Matsui

(10) Patent No.: US 7,761,246 B2
(45) Date of Patent: Jul. 20, 2010

(54) SURFACE INSPECTION METHOD AND SURFACE INSPECTION APPARATUS

(75) Inventor: Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/349,206

(22) Filed: Jan. 6, 2009

(65) Prior Publication Data

US 2009/0135413 A1 May 28, 2009

Related U.S. Application Data

(63) Continuation of application No. 11/826,088, filed on Jul. 12, 2007, now Pat. No. 7,487,049.

(30) Foreign Application Priority Data

Jul. 12, 2006 (JP) ............................. 2006-191055

(51) Int. Cl.
*G01N 21/88* (2006.01)

(52) U.S. Cl. .................. 702/40; 356/237.2; 356/237.5; 250/559.4; 250/221

(58) Field of Classification Search .................. 702/40; 356/237.1–237.2, 237.5; 250/559.42
See application file for complete search history.

(56) References Cited

U.S. PATENT DOCUMENTS

| 5,037,202 A | 8/1991 | Batchelder et al. |
| 5,469,259 A | 11/1995 | Golby et al. |
| 5,798,829 A | 8/1998 | Vaez-Iraavani |
| 6,762,831 B2 * | 7/2004 | Shibata et al. ........... 356/237.2 |

* cited by examiner

*Primary Examiner*—Drew A Dunn
*Assistant Examiner*—Hien X Vo
(74) *Attorney, Agent, or Firm*—McDermott Will & Emery LLP

(57) ABSTRACT

When detecting light scattered by an object to be inspected by using a pulse laser as a light source, noise increases unless a sampling repletion period of an A/D converter is determined so as to be related to a pulse oscillation repetition period of the light source. (1) The sampling repletion period of the A/D converter is set equal to the pulse oscillation repetition period of the light source or an integer times thereof, and the sampling is synchronized with oscillation of the light source. Or (2) the sampling repletion period of the A/D converter is set equal to a half-integer times the pulse oscillation repetition period of the light source. Even if a ripple component resulting from emission pulses of the light source remains in the scattered light signal supplied to the A/D converter remains, therefore, its influence can be eliminated or reduced.

3 Claims, 9 Drawing Sheets

FIG.2
SIDE VIEW
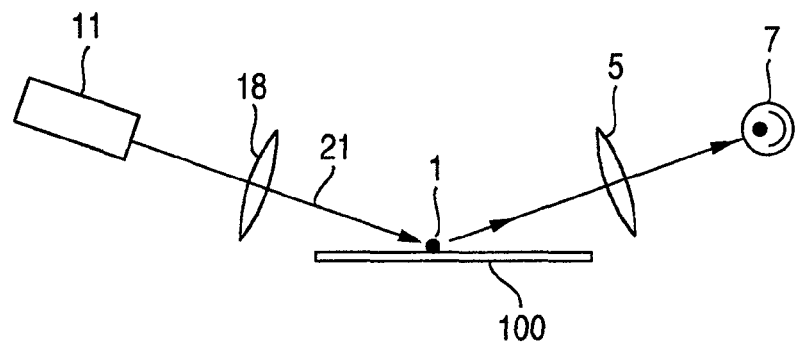
PLAN VIEW
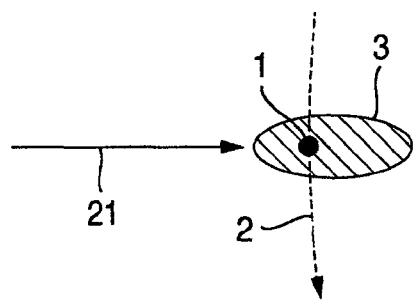
FIG.3
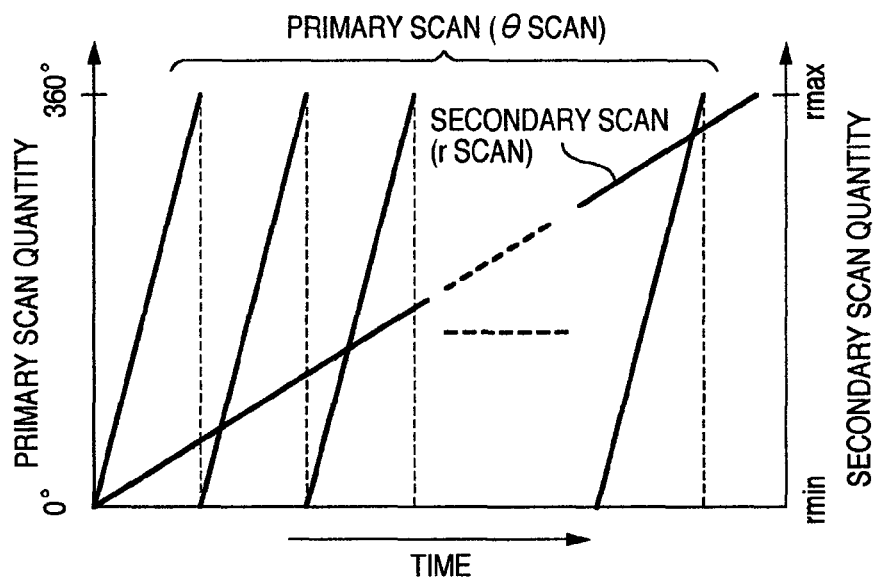

SAMPLING REPETITION PERIOD = 1 × PULSE OSCILLATION REPETITION PERIOD

SAMPLING REPETITION PERIOD = 1 × PULSE OSCILLATION REPETITION PERIOD

SAMPLING REPETITION PERIOD = 1 × PULSE OSCILLATION REPETITION PERIOD

SAMPLING REPETITION PERIOD = 0.97 × PULSE OSCILLATION REPETITION PERIOD

SAMPLING REPETITION PERIOD = 1.5 × PULSE OSCILLATION REPETITION PERIOD

SAMPLING REPETITION PERIOD = 1.5 × PULSE OSCILLATION REPETITION PERIOD

SAMPLING REPETITION PERIOD = 1.5 × PULSE OSCILLATION REPETITION PERIOD

SAMPLING REPETITION PERIOD = 1.45 × PULSE OSCILLATION REPETITION PERIOD

SAMPLING REPETITION PERIOD = 0.50 × PULSE OSCILLATION REPETITION PERIOD

SAMPLING REPETITION PERIOD = 0.50 × PULSE OSCILLATION REPETITION PERIOD

SAMPLING REPETITION PERIOD = 0.50 × PULSE OSCILLATION REPETITION PERIOD

SAMPLING REPETITION PERIOD = 0.48 × PULSE OSCILLATION REPETITION PERIOD

SAMPLING REPETITION
PERIOD = 2.5 × PULSE
OSCILLATION REPETITION
PERIOD

SAMPLING REPETITION
PERIOD = 2.5 × PULSE
OSCILLATION REPETITION
PERIOD

SAMPLING REPETITION
PERIOD = 2.5 × PULSE
OSCILLATION REPETITION
PERIOD

SAMPLING REPETITION
PERIOD = 2.4 × PULSE
OSCILLATION REPETITION
PERIOD

SAMPLING REPETITION PERIOD = 1.5 × PULSE OSCILLATION REPETITION PERIOD

SAMPLING REPETITION PERIOD = 1.5 × PULSE OSCILLATION REPETITION PERIOD

SAMPLING REPETITION PERIOD = 1.5 × PULSE OSCILLATION REPETITION PERIOD

SAMPLING REPETITION PERIOD = 1.3 × PULSE OSCILLATION REPETITION PERIOD

SURFACE INSPECTION METHOD AND SURFACE INSPECTION APPARATUS

RELATED APPLICATIONS

This application is a Continuation of U.S. Ser. No. 11/826,088, filed Jul. 12, 2007 now U.S. Pat. No. 7,487,049, claiming priority of Japanese Application No. 2006-191055, filed on Jul. 12, 2006, the entire contents of each of which are hereby incorporated by reference herein.

BACKGROUND OF THE INVENTION

The present invention relates to a surface inspection method and a surface inspection apparatus.

Conventionally, on a production line for a semiconductor substrates (semiconductor wafer), defects such as contaminant particles which have adhered to the surface of the substrate or scratches generated during working are inspected to monitor the dust generating situation of a production apparatus. For example, in the semiconductor substrate before circuit pattern forming, it is necessary to detect minute contaminant particles and defects as small as several nm or less on the surface. As for the inspection of the substrate surface, crystal defects existing in a shallow region near the substrate surface and surface roughness of the substrate surface also become subjects of the inspection, besides the above-described contaminant particles and defects. A technique for detecting minute defects on the surface of an object to be inspected such as a semiconductor substrate is described in, for example, U.S. Pat. No. 5,798,829. In other words, a semiconductor wafer or the like which is the inspection subject is mounted on an inspected object moving stage, and a partial region on the surface (illumination spot) is irradiated with illumination light generated by a laser light source. If in this state a contaminated particle which has adhered to the surface of the semiconductor wafer or a defect on the surface crosses the illumination spot, it generates scattered light. In the above-described conventional technique, the contaminated particle or defect is detected by catching the scattered light.

It is well known that if a contaminated particle or defect to be detected is sufficiently smaller than the illumination wavelength in the surface inspection apparatus described in the above-described conventional techniques intensity of light scattered by the contaminated particle or defect is proportional to approximately the sixth power of the particle size according to the Rayleigh scattering theory. It is also well known that the scattered light intensity is in inverse proportion to approximately the fourth power of the illumination wavelength according to the Rayleigh scattering theory. Until now, an Ar laser of 488 nm and a YAG second harmonic generation laser of 532 nm have been mainly used in the surface inspection apparatuses using the conventional techniques. However, higher sensitivity can be achieved by making the illumination length further shorter. By the way, in these laser light sources, there are a continuously oscillating CW laser and a pulse oscillating pulse laser depending upon the temporal form of emission. Although the Ar laser and the YAG second harmonic generation laser which have been mainly used are continuously oscillating type, there are a large number of pulse oscillating lasers in solid-state lasers having an oscillation wavelength in the ultraviolet region. An ultraviolet laser of 355 nm which is based on a YAG laser oscillating at 1064 nm and which utilizes its third harmonic (three times) generation is a representative one.

When using such a pulse laser in order to achieve the higher sensitivity, the following problem occurs. It is supposed that a pulse laser is used as the laser light source in the configuration of the surface inspection apparatus described in the conventional technique. In a typical pulse laser, for example, the repetition rate is in the range of approximately 50 to 180 MHz and the time width at half maximum of each emission pulse is in the range of approximately 10 to 30 ps. Except time delay caused by the length of the optical path, the scattered light at this time also has a temporal feature equivalent to the emission pulse of the laser light source, i.e., an equivalent repetition rate and an equivalent width at half maximum. A photomultiplier tube is typically used in a photodetector for detecting the scattered light. However, the time response characteristic of the photomultiplier tube is typically worse than the time width at half maximum of the pulse laser. As exemplified in FIG. 4, the time change waveform of the individual scattered light pulse in the output signal of the photomultiplier tube is largely distorted. Since the time response characteristic of the photomultiplier tube is approximately equal to or better than the repetition rate of the pulse laser, however, at least individual scattered light pulses are isolated and detected. An amplifier for amplifying the output signal of the photomultiplier tube needs to be narrow in bandwidth in order to reduce the shot noise component contained in the scattered light signal. On the other hand, a bandwidth needs to be broader than a definite width in order to find a detection position of a detected contaminated particle or defect accurately. In many cases, therefore, the bandwidth of the amplifier is typically set between DC and a frequency in the range of several MHz to several tens MHz. As a result of amplification in such a bandwidth, the scattered light pulses isolated and detected in the output signal of the photodetector are integrated to form a continuous waveform that nearly corresponds to an envelope of the scattered light pulses as exemplified in FIG. 4. However, the bandwidth of the amplifier is not wide enough to completely integrate and remove the original pulse trains. When an expanded output waveform of the amplifier is viewed, a ripple component caused by the original pulse train remains. It is apparent that the ripple component causes noise in the scattered light intensity signal. The detection sensitivity for contaminated particles or defects is thus lowered.

SUMMARY OF THE INVENTION

An object of the present invention is to prevent the detected light signal intensity from being affected by the remaining ripple component resulting from pulse oscillation in the light source, or reduce the influence of the remaining ripple component, even when a pulse oscillating light source is used.

In accordance with a first aspect, the present invention provides a surface inspection method for detecting contaminated particles or defects existing on a surface of an object to be inspected or inside near the surface, by using an object to be inspected moving stage for moving the object to be inspected, a pulse laser light source for conducting pulse oscillation repetitively in time, illumination means for irradiating an illumination spot having a predetermined size on the surface of the object to be inspected with pulse light supplied from the light source, scattered/diffracted/reflected light detection means for detecting light generated by scattering/diffracting/reflecting the irradiating light in the illumination spot and converting the light to an electric signal, A/D conversion means for converting the electric signal to digital data, and particle size calculation means for calculating a size of a contaminated particle or defect on the basis of the digital data, wherein the A/D conversion means samples the electric signal at substantially constant sampling intervals, and the sampling interval is determined so as to be associated with a pulse oscillation repetition period of the laser light source.

In accordance with another aspect, the present invention provides a surface inspection apparatus for detecting contaminated particles or defects existing on a surface of an object to be inspected or inside near the surface, the surface inspection apparatus including an object to be inspected moving stage for moving the object to be inspected, a pulse laser light source for conducting pulse oscillation repetitively in time, an illumination optics for irradiating an illumination spot having a predetermined size on the surface of the object to be inspected with pulse light supplied from the light source, a scattered/diffracted/reflected light detection system for detecting light generated by scattering/diffracting/reflecting the irradiating light in the illumination spot and converting the light to an electric signal, an A/D conversion system for converting the electric signal to digital data, and a particle size calculation system for calculating a size of a contaminated particle or defect on the basis of the digital data, wherein a maximum response frequency of the scattered/diffracted/reflected light detection system is set to be lower than a repetition rate of the pulse laser light source, and the A/D conversion system is configured to have a sampling interval that is equal to approximately a half-integer times inclusive of approximately ½ times as long as a pulse oscillation repetition period of the pulse laser light source.

In accordance with still another aspect, the present invention provides a surface inspection method including moving the object to be inspected, irradiating a surface of the object to be inspected with pulse light supplied from a light source which conducts pulse oscillation repetitively in time, detecting light generated by at least any of scattering, diffracting and reflecting the irradiating light on the surface of the object to be inspected and converting the light to an electric signal, converting the electric signal to digital data, calculating a size of a contaminated particle or defect on the basis of the digital data, and detecting a contaminated particle or defect existing on the surface of the object to be inspected or inside near the surface, wherein when converting the electric signal to digital data, the electric signal is sampled at substantially constant sampling intervals, and the sampling interval is determined so as to be associated with a pulse oscillation repetition period of the light source.

In accordance with still another aspect, the present invention provides a surface inspection apparatus including an object to be inspected moving stage for moving an object to be inspected, a light source for conducting pulse oscillation repetitively in time, an illumination optics for irradiating an illumination spot having a predetermined size on a surface of the object to be inspected with pulse light supplied from the light source, a photodetector system for detecting light generated by scattering/diffracting/reflecting the irradiating light in the illumination spot and converting the light to an electric signal, an A/D conversion system for converting the electric signal to digital data, a particle size calculation system for calculating a size of a contaminated particle or defect on the basis of the digital data, and a sampling controller for controlling a sampling interval of the A/D conversion system on the basis of a pulse oscillation repetition period of the light source.

Aspects of the present invention are not restricted to the above-described aspects, but are made clear from descriptions in claims, the specification and drawings.

Even if the ripple component caused by light emission pulses of the light source remains in the light signal supplied from the inspected object, it becomes possible, according to the present invention, to eliminate or reduce its influence.

Other objects, features and advantages of the invention will become apparent from the following description of the embodiments of the invention taken in conjunction with the accompanying drawings.

BRIEF DESCRIPTION OF THE DRAWINGS

FIG. 2 is a diagram showing a configuration of optics according to the first embodiment of the present invention;

FIG. 3 is a diagram showing a helical scan drive method of an inspected object moving stage according to the first embodiment of the present invention;

DESCRIPTION OF THE INVENTION

Figure 1:
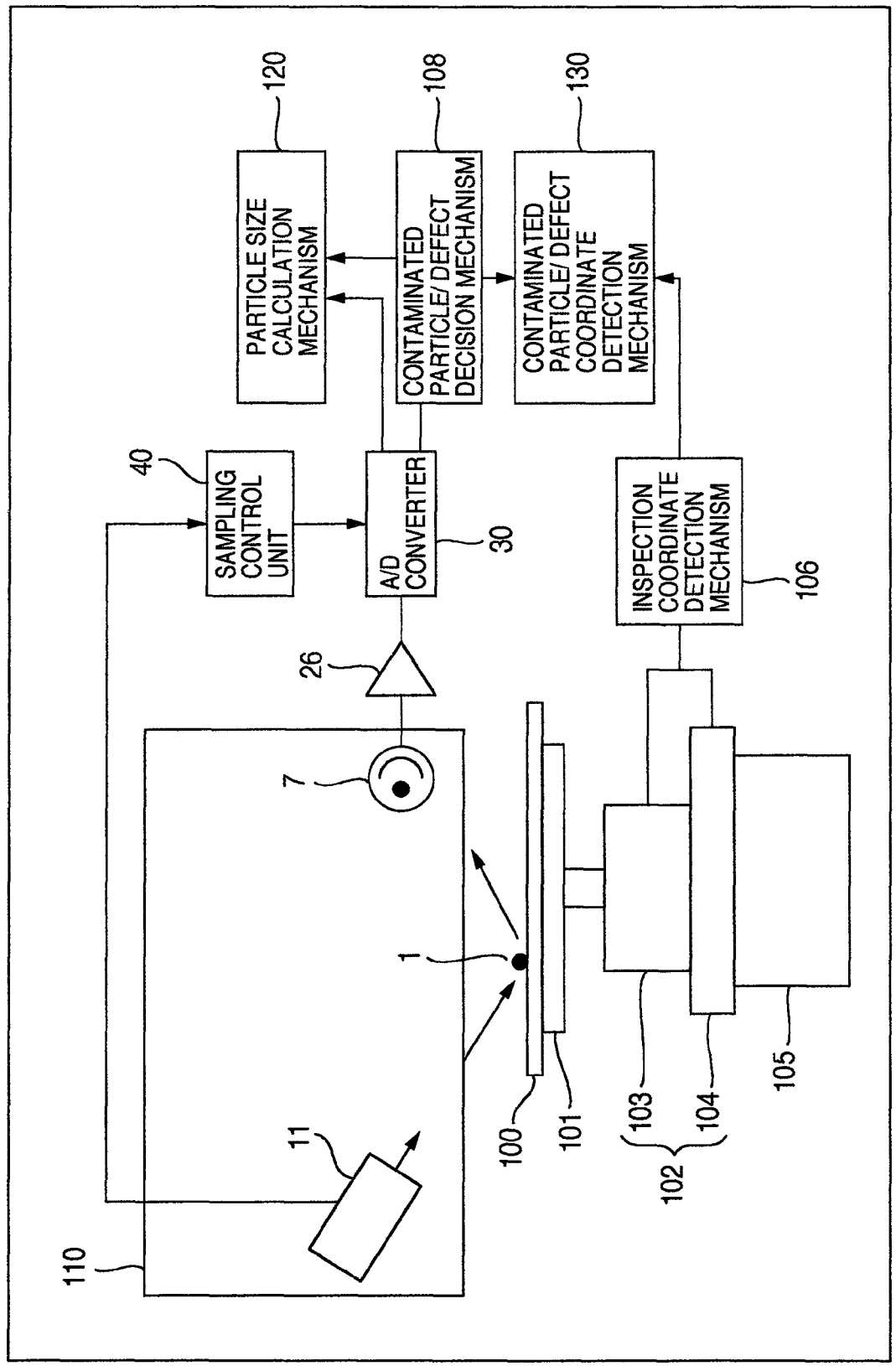
FIG. 1 is a diagram showing a configuration of a surface inspection apparatus according to a first embodiment of the present invention.

The present invention relates to a technique for detecting a minute contaminated particle or defect when it is present on, for example, a semiconductor substrate (semiconductor wafer), and a technique for measuring information concerning surface roughness of the substrate. In particular, the present invention relates to a surface inspection technique for inspecting the substrate surface by using a pulse laser, which performs pulse oscillation repetitively in time, as the light source.

A surface inspection apparatus according to an embodiment of the present invention includes an object to be inspected moving stage, a pulse laser light source, illumination means for irradiating an illumination region having a predetermined size on the surface of an object to be inspected with laser light emitted from the pulse laser light source, scattered/diffracted/reflected light collecting means for collecting light generated by scattering/diffracting/reflecting the irradiated light in the illumination region, scattered/diffracted/reflected light detection means for detecting the focused scattered/diffracted/reflected light and converting it to an electric signal, A/D conversion means for converting the electric signal to digital data, particle size calculation means for calculating the size of a contaminated particle or defect on the basis of the digital data, and contaminated particle/defect coordinate calculation means for calculating position coordinate values of the contaminated particle/defect on the surface of the object to be inspected. The surface inspection apparatus according to an embodiment of the present invention has, for example, the following features.

(Feature 1) The A/D conversion means is configured to sample the electric signal at nearly constant sampling time intervals. The sampling time interval is determined so as to be associated with the pulse oscillation repetition period of the pulse laser light source.

(Feature 2) In more detail, the following technique is included. The sampling time interval of the A/D conversion means is made equal to or an integer times the pulse oscillation repetition period of the pulse laser light source. In addition, the sampling in the A/D conversion means is synchronized with the pulse oscillation of the pulse laser light source.

(Feature 3) An alternative technique has the following features 3 to 5. The A/D conversion means is configured so as to have a sampling time interval that is equal to approximately a half-integer times, inclusive of approximately half, the pulse oscillation repetition period of the pulse laser light source.

(Feature 4) The particle size calculation means calculates the size of the contaminated particle or defect on the basis of the digital data at two or more points adjacent in time sampled by the A/D conversion means.

(Feature 5) The processing of the digital data at two more points includes a technique of minimizing the influence of the ripple component resulting from the emission pulse train supplied from the pulse laser light source and included in the electrical signal obtained from the scattered/diffracted/reflected light detection means.

(Feature 6) The digital data processing includes a technique of conducting addition or averaging on the digital data at the two points.

(Feature 7) The digital data processing includes a technique of conducting weighted addition or weighted averaging on the digital data at three or more points.

Hereafter, embodiments of the present invention will be described in more detail with reference to the drawings.

FIG. 1 shows a first embodiment of a contaminated particle/defect inspection apparatus using the contaminated particle/defect inspection method according to the present invention. A semiconductor wafer 100 which is the object to be inspected is vacuum-adsorbed to a chuck 101. The chuck 101 is mounted on an object to be inspected moving stage 102, which includes a rotation stage 103 and a translation stage 104, and a Z-stage 105. Illumination/detection optics 110 is disposed above the semiconductor wafer 100.

The illumination/detection optics 110 will now be described with reference to FIG. 2. A pulse laser which causes pulse oscillation of light having a wavelength in the ultraviolet region repetitively in time is used as a light source 11 of the illumination light. In the present embodiment, a pulse laser having an oscillation wavelength of 355 nm as a third harmonic wave of the YAG laser, a repetition rate in the range of approximately 50 to 150 MHz, and a time width at half maximum of each light emission pulse in the range of approximately 10 to 30 ps is used. Pulse light emitted from the light source 11 is incident on the semiconductor wafer 100 as an irradiation beam 21 via an illumination lens 18 to form an illumination spot 3 having a predetermined size. The illumination light is, for example, light of P polarization. The illumination light is incident obliquely onto the surface of the semiconductor wafer 100, which is the object to be inspected, at approximately a Brewster angle to crystal Si. Therefore, the illumination spot 3 nearly takes the shape of an ellipse. The inside of a contour line in which the illuminance falls to the inverse of the square of e (where e is the base of natural logarithms) in the central part of the illumination spot is re-defined as illumination spot. The width of this illumination spot in the major axis direction is denoted by d1 and the width of the illumination spot in the minor axis direction is denoted by d2. As shown in FIG. 3, the object to be inspected moving stage 102 changes the rotation movement θ which is the primary scan and the translation movement r which is the secondary scan in combination with time, and thereby causes nearly the whole surface of the semiconductor wafer 100 to be relatively scanned with the illumination spot 3 spirally. While the rotation stage makes one revolution, the secondary scan moves by Δr. If Δr>d1, a gap region which is not irradiated with illumination light and which is not inspected in the helical scan is formed on the semiconductor wafer 100. Typically, therefore, Δr is set so as to satisfy the relation Δr<d1. In the present embodiment, the scan with the illumination spot 3 is conducted from an inner circumference toward an outer circumference of the semiconductor wafer 100. However, the converse may also be adopted. In the present embodiment, the rotation stage 103 is driven at a nearly constant angular velocity and the translation stage 103 is driven at a nearly constant linear velocity, in the nearly whole region ranging from the inner circumference to the outer circumference of the semiconductor wafer 100. An inspection coordinate detection mechanism 106 is attached to the object to be inspected moving stage 102 in order to detect a primary scan coordinate position θ and a secondary scan coordinate position r in the inspection. In the present embodiment, an optical reading rotary encoder is used to detect the primary scan coordinate position θ and an optical reading linear encoder is used to detect the secondary scan coordinate position r. For both of them, sensors according to a different detection principle may also be used, as long as sensors can detect the angle or the position on the straight line with high precision. A condenser lens 5 has a configuration capable of collecting scattered light at a low elevation angle to capture light scattered by a minute contaminated particle according to the Rayleigh scattering with a high efficiency. In this configuration, a contaminated particle 1 passes through the illumination spot 3 as represented by a moving locus 2 of the contaminated particle in a plan view shown in FIG. 2. As a result, a scattered light signal is obtained from a photodetector 7. In the present embodiment, a photomultiplier tube is used as the photodetector 7. However, a photodetector based on a different detection principle may also be used as long as the photodetector can detect light scattered by the contaminated particle with high sensitivity. As shown in FIG. 1, the scattered light signal supplied from the photodetector 7 is amplified by an amplifier 26, then sampled by an A/D converter 30, and converted to digital data. Since the light source 11 is a pulse laser, the scattered light incident on the photodetector 7 also has a temporal feature equivalent to that of the light pulses emitted from the light source 11, i.e. equivalent repetition rate and an equivalent width at half maximum, except the time delay resulting from the length of the optical path through which the scattered light passes.

Figure 4:
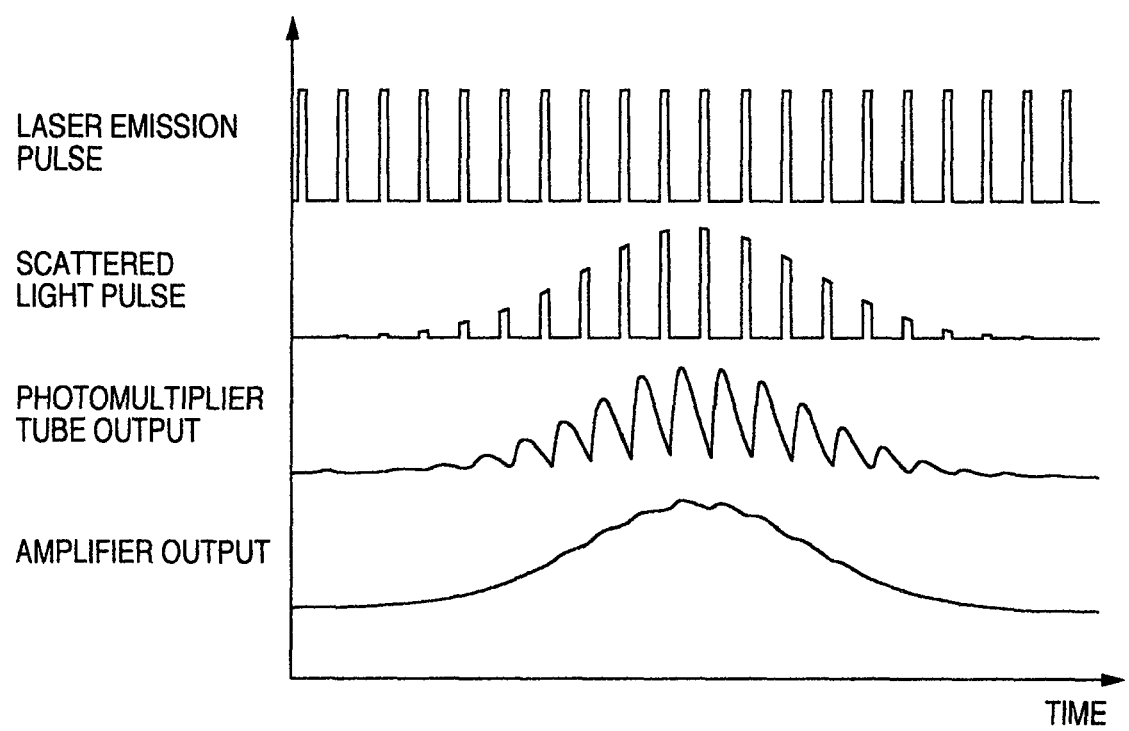
FIG. 4 is a diagram showing signal waveforms obtained in the surface instruction apparatus according to the first embodiment of the present invention.

As shown in FIG. 4, the time response characteristic of the photomultiplier tube in the photodetector 7 is worse than the time width at half maximum. In the output signal, therefore, time change waveforms of individual scattered light pulses are remarkably deformed. However, the time response characteristic of the photomultiplier tube is nearly equivalent to or better than the oscillation repetition rate of the pulse laser. Therefore, at least individual scattered light pulses are isolated and detected. In FIG. 4, the light source 11 performs pulse emission approximately ten times while the contaminated particle 1 passes through the illumination spot 3. As for the number of times of the pulse emission, a difference, such as surplus or deficiency of approximately one pulse, inevitably occurs depending upon the timing at which the contaminated particle 1 enters the illumination spot 3. If the number of times of pulse emission generated while the contaminated particle 1 passes through the illumination spot 3 is small, a relative error of the error corresponding to the number of pulses to the number of all pulses becomes large. As for the relation between the pulse repetition rate of the light source 11 and the time taken for the contaminated particle 1 to pass through the illumination spot 3, therefore, it is desirable that pulse emission is generated at least five times during this time. It is necessary to make the bandwidth of the amplifier 26 narrow to reduce the shot noise component contained in the scattered light signal. On the other hand, however, for finding the detection position of the contaminated particle/defect accurately, it is not desirable to make the bandwidth too narrow, because the distortion of the scattered light signal waveform becomes large. Thus, it is proper that the bandwidth of the amplifier 26 should be typically set between DC and a frequency in the range of several MHz to several tens MHz. In the present embodiment, the bandwidth of the amplifier 26 is set between DC and approximately 30 MHz. As a result of amplification with such a bandwidth, scattered light pulses isolated and detected in the output signal of the photodetector 7 are integrated, resulting in a continuous waveform nearly corresponding to their envelop line as shown in FIG. 4. However, the bandwidth of the amplifier 26 is not a bandwidth with which the original pulse train can be completely integrated and removed. Viewing an expanded output waveform of the amplifier 26, therefore, the ripple component resulting from the original pulse train remains. It is apparent that the ripple component causes noise when sampling is conducted in the subsequent A/D converter 30. For example, the case where the output signal is sampled at completely the same repetition period as the original repetition period of the pulse laser will now be described.

Figure 5A:
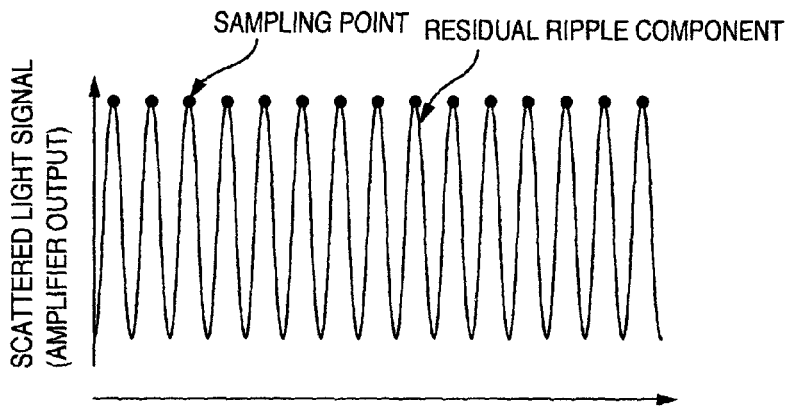
FIG. 5A is a diagram for explaining data obtained when a signal waveform is sampled with a repetition period equal to a repetition period of a pulse laser in the first embodiment of the present invention.
Figure 5B:
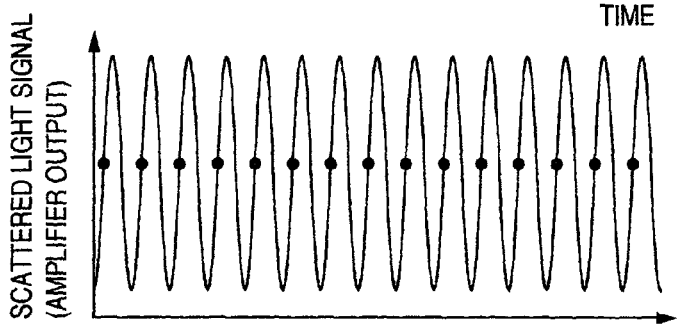
FIG. 5B is a diagram for explaining data obtained when the signal waveform is sampled with a repetition period equal to the repetition period of the pulse laser in the first embodiment of the present invention.
Figure 5C:
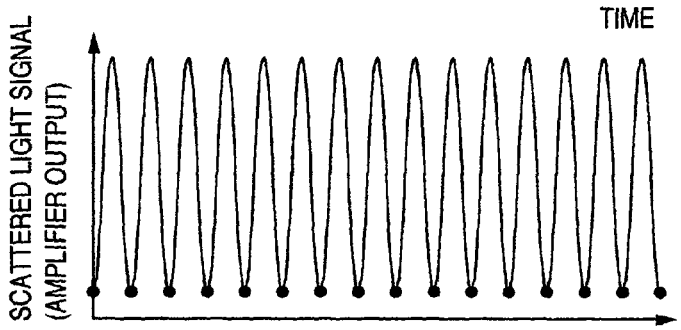
FIG. 5C is a diagram for explaining data obtained when the signal waveform is sampled with a repetition period equal to the repetition period of the pulse laser in the first embodiment of the present invention.
Figure 5D:
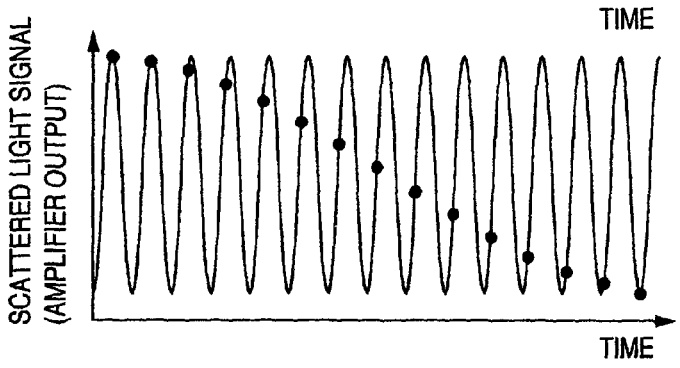
FIG. 5D is a diagram for explaining data obtained when the signal waveform is sampled with a repetition period equal to the repetition period of the pulse laser in the first embodiment of the present invention.

FIGS. 5A to 5D are diagrams for explaining data obtained when sampling the signal waveform with a repetition period equal to the repetition period of the pulse laser. The abscissa indicates time, and the ordinate indicates the intensity of the scattered light signal (amplifier output). If the sampling phase differs at this time as shown in FIGS. 5A to 5C, sampling is conducted in different phase positions of the ripple component. Therefore, errors resulting from the ripple component are contained in the sampling result. In addition, paying attention to certain one sampling data point (corresponding to one of sampling points represented by black dots (●) in FIGS. 5A to 5C), the output signal has also nearly the same value at sampling data points before and after the certain one sampling data point. Therefore, it is apparent that the errors cannot be improved even if addition or averaging is conducted on a plurality of sampling data. The case where the output signal is sampled with a repetition period that is slightly different from the original repetition period of the pulse laser will now be considered. (In FIG. 5D, the sampling repetition period is 0.97 times the pulse oscillation repetition period.) In this case, the sampling phase relative to the signal waveform shifts with time as indicated by sampling points represented by black dots (●) in FIG. 5D. Therefore, errors resulting from the ripple component are still contained in the sampling results. It is apparent that the phenomena shown in FIGS. 5A to 5D occur in the same way not only when the sampling repetition period is equal to the original repetition period of the pulse laser, but also when the sampling repetition period is equal to an integer times the original repetition period of the pulse laser. If the sampling repetition period is chosen to be equal to the original repetition period of the pulse laser or integer times the original repetition period of the pulse laser, it is thus necessary to completely synchronize the sampling repetition period with the original repetition period of the pulse laser in order to reduce the influence of the residual ripple component resulting from the original light emission pulse train.

In the configuration of the present embodiment shown in FIG. 1, therefore, a pulse oscillation synchronizing signal is obtained from the light source 11, and a sampling control unit 40 generates a sampling control signal by using the pulse oscillation synchronizing signal as it is or dividing the pulse oscillation synchronizing signal in frequency to a reciprocal of an integer. The A/D converter 30 conducts sampling on the basis of the sampling control signal. Subsequently, a contaminated particle/defect decision mechanism 108 compares digital data corresponding to the scattered light intensity obtained from the A/D converter 30 with a predetermined detection threshold. If the scattered light intensity value is at least the threshold, the contaminated particle/defect decision mechanism 108 generates contaminated particle/defect decision information. Upon generation of the contaminated particle/defect decision information, a contaminated particle/defect coordinate detection mechanism 130 calculates a coordinate position of the detected contaminated particle/defect on the basis of information supplied from the inspection coordinate detection mechanism 106. A particle size calculation mechanism 120 calculates the size of the detected contaminated particle/defect on the basis of the scattered light intensity value.

Thus, in the present embodiment, the timing at which the A/D converter 30 samples the output waveform of the amplifier 26 is always synchronized with the scattered light pulses. Therefore, it is possible to avoid picking up errors caused by the residual ripple component as shown in FIGS. 5A to 5D as main noise causes.

In the present embodiment, the object to be inspected moving stage 102 is driven with a nearly constant angular velocity. Even if the object to be inspected moving stage 102 is driven with a nearly constant linear velocity, however, there is no change in resulting effect.

Figure 6:
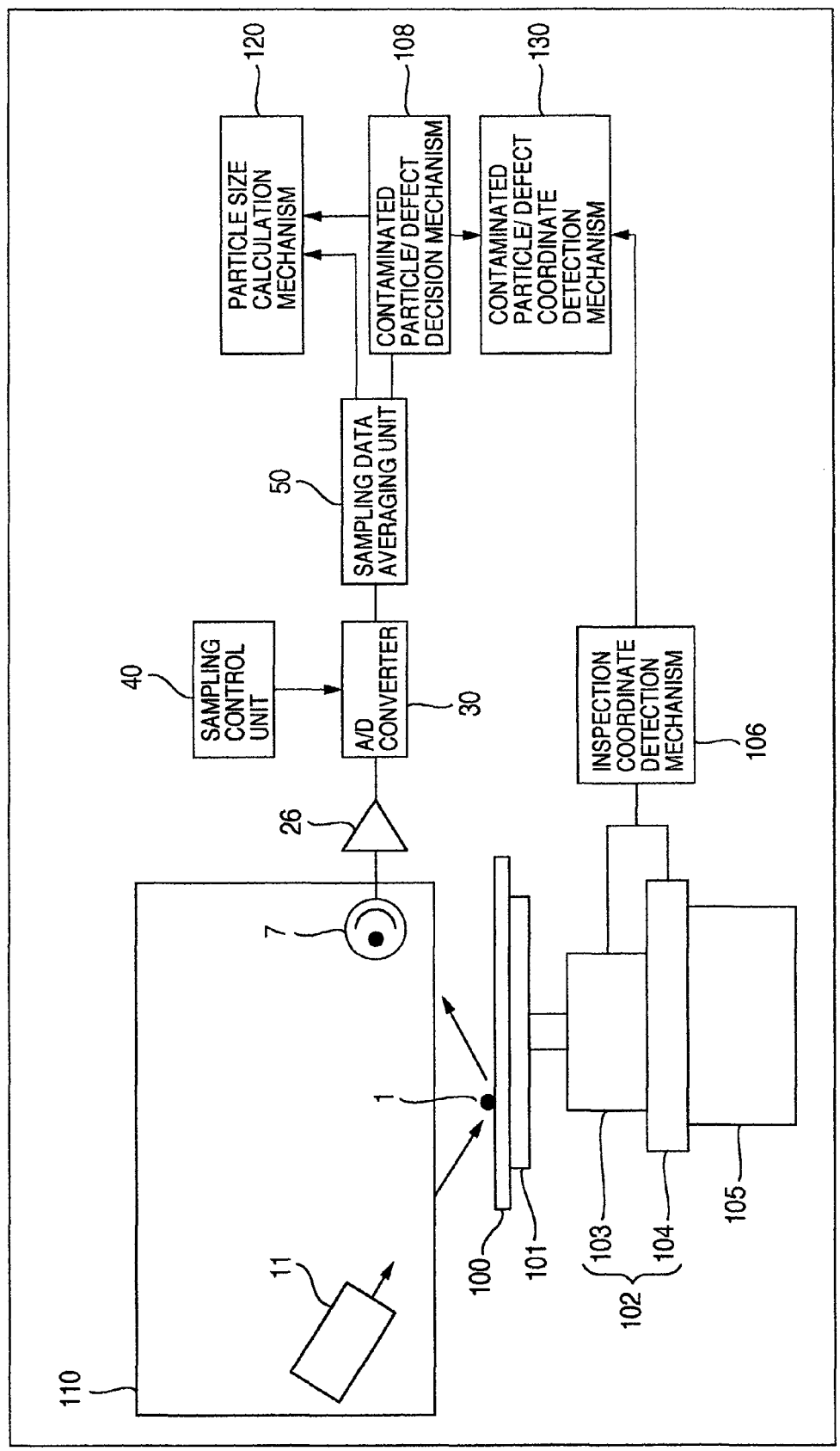
FIG. 6 is a diagram showing a configuration of a surface inspection apparatus according to a second embodiment of the present invention.

A second embodiment using a different configuration according to the present invention will now be described with reference to FIG. 6. Since other parts except the sampling control unit 40 and a sampling data averaging unit 50 are equivalent to those in the first embodiment, description of them will be omitted.

Figure 7A:
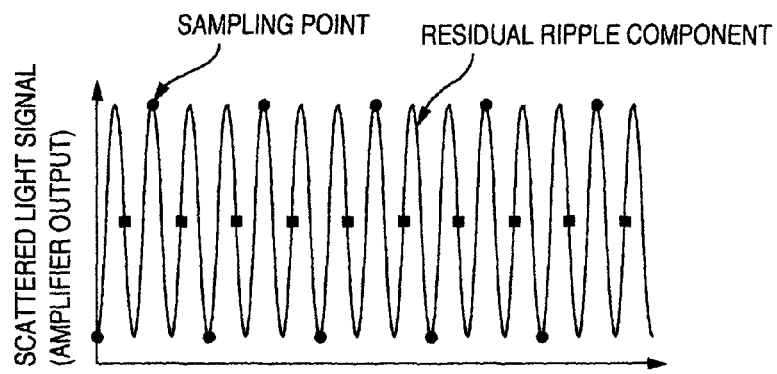
FIG. 7A is a diagram for explaining data obtained when a signal waveform is sampled with a repetition period as long as 1.5 times a repetition period of a pulse laser in an embodiment of the present invention.
Figure 7B:
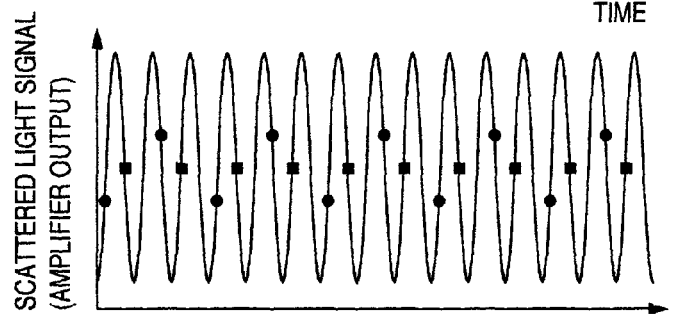
FIG. 7B is a diagram for explaining data obtained when the signal waveform is sampled with a repetition period as long as 1.5 times the repetition period of the pulse laser in the embodiment of the present invention.
Figure 7C:
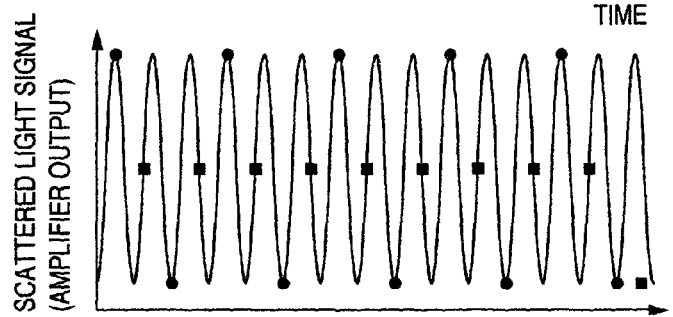
FIG. 7C is a diagram for explaining data obtained when the signal waveform is sampled with a repetition period as long as 1.5 times the repetition period of the pulse laser in the embodiment of the present invention.
Figure 7D:
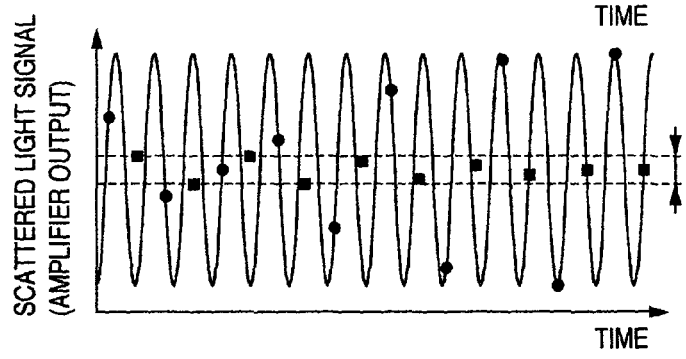
FIG. 7D is a diagram for explaining data obtained when the signal waveform is sampled with a repetition period as long as 1.5 times the repetition period of the pulse laser in the embodiment of the present invention.

In a configuration of the present embodiment, a pulse oscillation synchronizing signal is obtained from the light source 11, and a sampling control unit 40 generates a sampling control signal having a repetition period that is 1.5 times as long as the repetition period of the pulse laser in the light source 11. The A/D converter 30 conducts sampling on the basis of the sampling control signal. At this time, results of sampling conducted at sampling points represented by black dots (●) in FIGS. 7A to 7C are obtained from the A/D converter 30, depending upon difference in sampling phase. In each of FIGS. 7A to 7C, each of data obtained by averaging values at two sampling data points that are adjacent in time in the results is represented by a black square (■). Variations of data values represented by black squares (■) are very small as compared with the amplitude of residual ripple component, and the data values vary little. It is appreciated that the influence of the residual ripple component resulting from the original light emission pulse train can be suppressed. The case where the output signal is sampled with a repetition period slightly different from 1.5 times the original repetition period of the pulse laser will now be considered. (In FIG. 7D, the sampling repetition period is 1.45 times the pulse oscillation repetition period.) In this case, the digital data train obtained from the A/D converter 30 varies largely from a maximum value to a minimum value of the residual ripple component with time elapse as represented by black dots in FIG. 7D. Variation of data values obtained by averaging values at two sampling data points that are adjacent in time in the results in the same way as the first embodiment and represented by black squares (■) are very small in the same way, as compared with the amplitude of the residual ripple component. (The amplitude of the variation of the data values is represented by arrows.) It is thus appreciated that the influence of the residual ripple component resulting from the original light emission pulse train has been successfully suppressed. Based on the effect, the sampling data averaging unit 50 in the configuration of the present embodiment calculates an average value at every two sampling data points that are adjacent in time in the digital data train obtained from the A/D converter 30.

Thus, in the present embodiment, the repetition period at which the A/D converter 30 samples the output waveform of the amplifier 26 is set equal to 1.5 times the original repetition period of the pulse laser, and averaging values at two data points that are adjacent in time is conducted for sampled data points. As a result, it becomes possible to avoid picking up errors caused by the residual ripple component as main causes of noise.

Figure 8A:
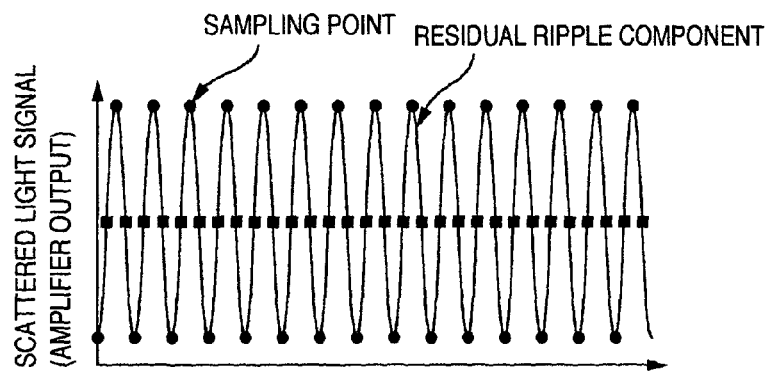
FIG. 8A is a diagram for explaining data obtained when a signal waveform is sampled with a repetition period as long as 0.5 times an repetition period of a pulse laser in an embodiment of the present invention.
Figure 8B:
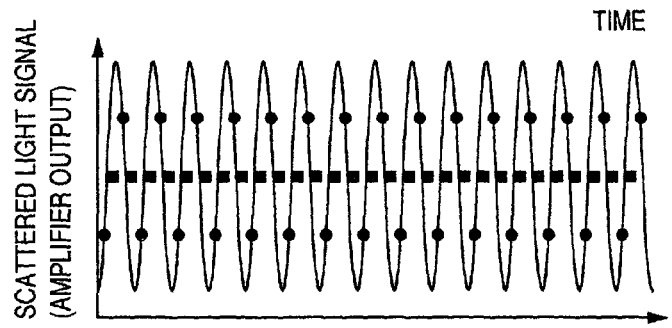
FIG. 8B is a diagram for explaining data obtained when the signal waveform is sampled with a repetition period as long as 0.5 times the repetition period of the pulse laser in the embodiment of the present invention.
Figure 8C:
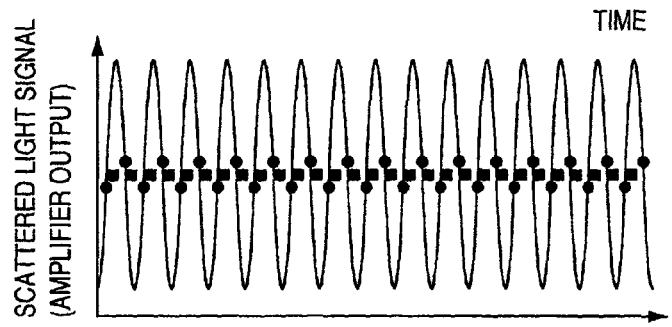
FIG. 8C is a diagram for explaining data obtained when the signal waveform is sampled with a repetition period as long as 0.5 times the repetition period of the pulse laser in the embodiment of the present invention.
Figure 8D:
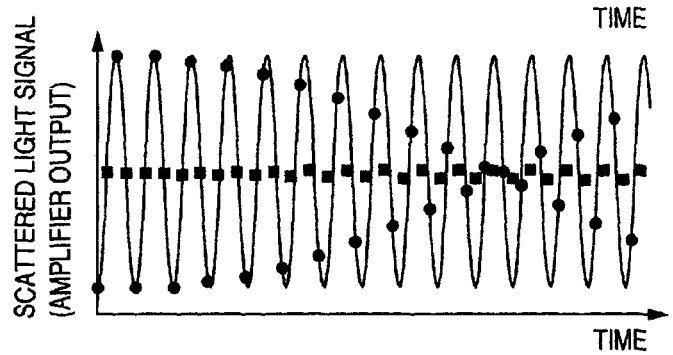
FIG. 8D is a diagram for explaining data obtained when the signal waveform is sampled with a repetition period as long as 0.5 times the repetition period of the pulse laser in the embodiment of the present invention.
Figure 9A:
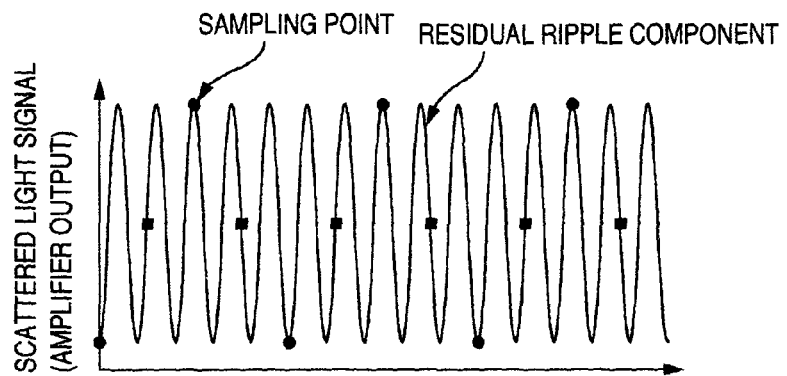
FIG. 9A is a diagram for explaining data obtained when a signal waveform is sampled with a repetition period as long as 2.5 times a repetition period of a pulse laser in an embodiment of the present invention.
Figure 9B:
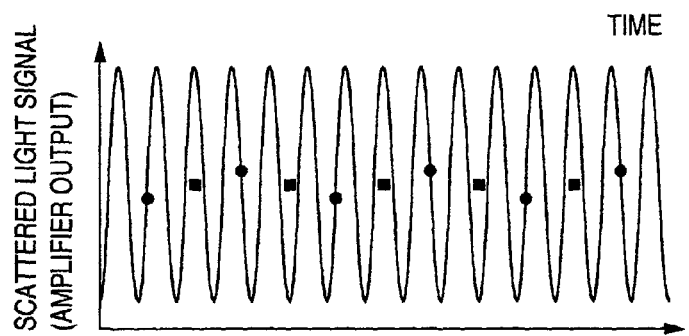
FIG. 9B is a diagram for explaining data obtained when the signal waveform is sampled with a repetition period as long as 2.5 times the repetition period of the pulse laser in the embodiment of the present invention.
Figure 9C:
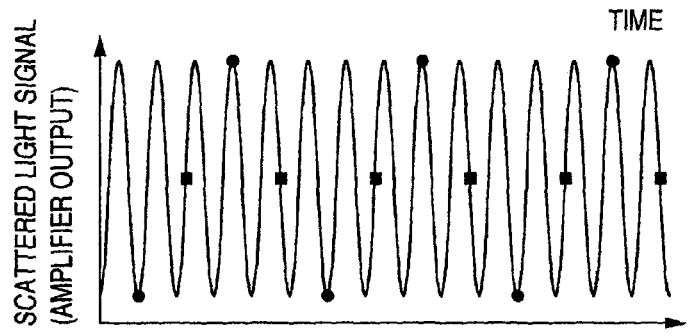
FIG. 9C is a diagram for explaining data obtained when the signal waveform is sampled with a repetition period as long as 2.5 times the repetition period of the pulse laser in the embodiment of the present invention.
Figure 9D:
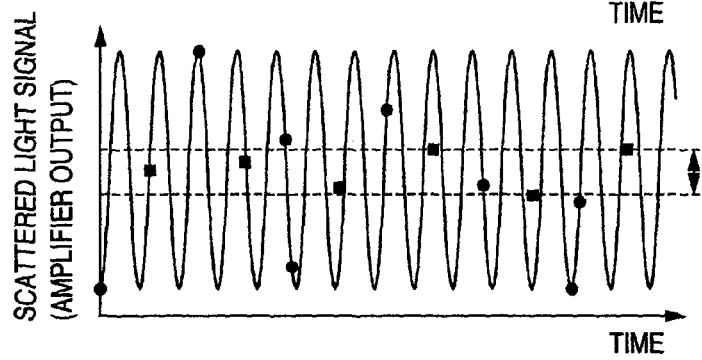
FIG. 9D is a diagram for explaining data obtained when the signal waveform is sampled with a repetition period as long as 2.5 times the repetition period of the pulse laser in the embodiment of the present invention.

Although in the present embodiment the sampling repetition period of the A/D converter 30 is set equal to 1.5 times the original repetition period of the pulse laser, similar effects are obtained even if a half-integer times such as 0.5 times or 2.5 times is used. For example, FIGS. 8A to 8C show the case of 0.5 times. FIG. 8D shows an example in which the output signal is sampled with a repetition period slightly different from 0.5 times the original repetition period of the pulse laser. (The sampling repetition period is set equal to 0.48 times the pulse oscillation repetition period.) FIGS. 9A to 9C show the case of 2.5 times. FIG. 9D shows an example in which the output signal is sampled with a repetition period slightly different from 2.5 times the original repetition period of the pulse laser. (The sampling repetition period is set equal to 2.4 times the pulse oscillation repetition period.)

Figure 10A:
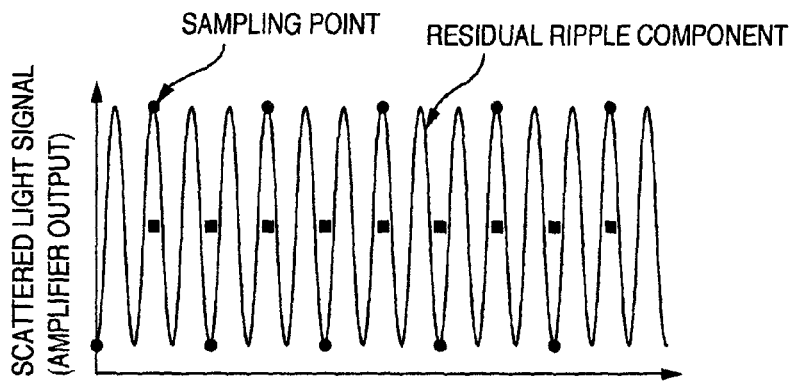
FIG. 10A is a diagram showing different data processing conducted on data obtained by sampling a signal waveform with a repetition period as long as 1.5 times the repetition period of the pulse laser in an embodiment of the present invention.
Figure 10B:
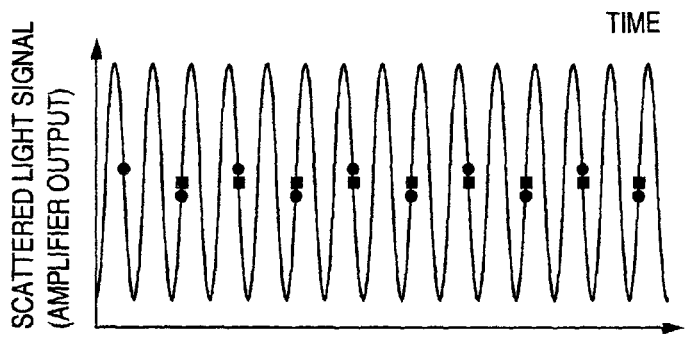
FIG. 10B is a diagram showing different data processing conducted on data obtained by sampling the signal waveform at the repetition period as long as 1.5 times the repetition period of the pulse laser in the embodiment of the present invention.
Figure 10C:
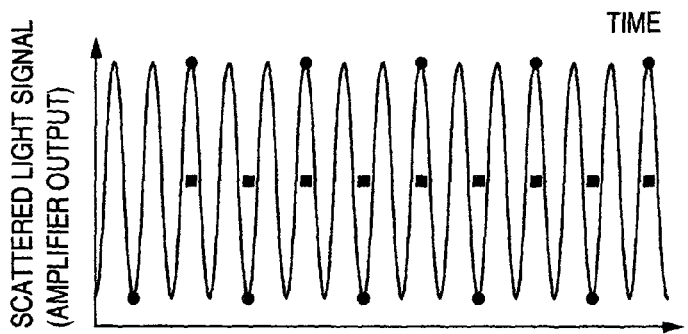
FIG. 10C is a diagram showing different data processing conducted on data obtained by sampling the signal waveform at the repetition period as long as 1.5 times the repetition period of the pulse laser in the embodiment of the present invention.
Figure 10D:
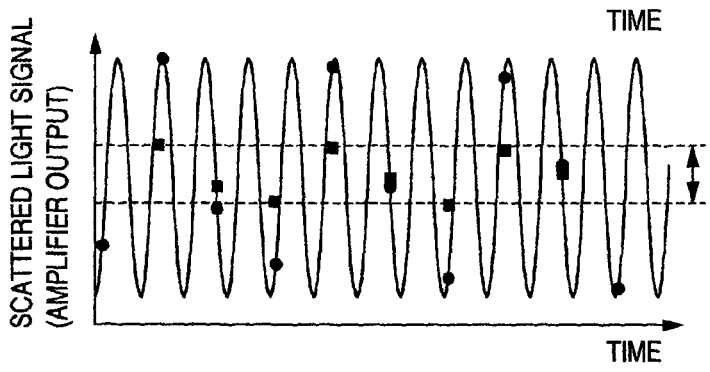
FIG. 10D is a diagram showing different data processing conducted on data obtained by sampling the signal waveform at the repetition period as long as 1.5 times the repetition period of the pulse laser in the embodiment of the present invention.

In the present embodiment, averaging values at two data points that are adjacent in time is conducted for sampled data points. As a matter of course, however, weighted addition or weighted averaging may be conducted on at least three data points that are adjacent in time. Denoting values at three adjacent data points by $A_{-1}$, $A_0$ and $A_{+1}$, the weighted averaging of values at three adjacent data points can be implemented by using, for example, $(0.5 \times A_{-1} + 1 \times A_0 + 0.5 \times A_{+1})/2$. In this case, results obtained when the sampling repetition period of the A/D converter 30 is set equal to 1.5 times the original repetition period of the pulse laser are shown in FIGS. 10A to 10C. Results obtained when the sampling repetition period of the A/D converter 30 is set equal to 1.3 times, which is slightly different from 1.5 times, the original repetition period of the pulse laser are shown in FIG. 10D.

According to the embodiment of the present invention, the sampling repetition period of the A/D converter is set equal to the pulse repetition period of the light source or set equal to an integer times the pulse oscillation repetition period of the light source and sampling is synchronized with the oscillation of the light source, or sampling is conducted with a repetition period equal to a half-integer times the pulse oscillation repetition period of the light source and then values at sampling data points that are adjacent in time are averaged. Even if the ripple component resulting from a light emission pulse of the light source remains in the scattered light signal supplied to the A/D converter, therefore, it becomes possible to eliminate or reduce its influence.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An optical inspection apparatus for inspecting an object to be inspected, the optical inspection apparatus comprising:
   a pulse light source;
   a light detection system which detects light from the object and converts the light to an electric signal;
   a conversion system which converts the electric signal to digital data; wherein:
   the conversion system is configured to have a sampling interval that is equal to approximately a half-integer times, inclusive of approximately ½ times, as long as a pulse oscillation repetition period of the pulse light source.

2. An optical inspection method comprising:
   irradiating an object to be inspected with pulse light supplied from a light source which conducts pulse oscillation repetitively in time;
   detecting light from the object to be inspected and converting the light to an electric signal; and
   converting the electric signal to digital data, wherein:
   when converting the electric signal to digital data, the electric signal is sampled at a predetermined sampling interval, and
   the sampling interval is equal to approximately a half-integer times, inclusive of approximately ½ times, as long as a pulse oscillation repetition period of the pulse light.

3. An optical inspection apparatus comprising:
   a pulse light source;
   a photodetector system which detects light from an object and converts the light to an electric signal;
   a conversion system which converts the electric signal to digital data; and
   a sampling controller for controlling a sampling interval of the conversion system on the basis of approximately a half-integer times, inclusive of approximately ½ times, as long as a pulse oscillation repetition period of the pulse light source.

* * * * *